US012708683B2

(12) United States Patent
Harris

(10) Patent No.: US 12,708,683 B2
(45) Date of Patent: Aug. 18, 2026

(54) SURFACE DISINFECTION WITH $PR^{3+}$ DOPED INORGANIC PHOSPHORS

(71) Applicant: THE BOEING COMPANY, Arlington, VA (US)

(72) Inventor: John N. Harris, Seattle, WA (US)

(73) Assignee: THE BOEING COMPANY, Arlington, VA (US)

( * ) Notice: Subject to any disclaimer, the term of this patent is extended or adjusted under 35 U.S.C. 154(b) by 405 days.

(21) Appl. No.: 18/326,338

(22) Filed: May 31, 2023

(65) Prior Publication Data

US 2023/0405158 A1 Dec. 21, 2023

Related U.S. Application Data

(60) Provisional application No. 63/366,576, filed on Jun. 17, 2022.

(51) Int. Cl.
*A61L 2/088* (2026.01)
*A61L 103/05* (2026.01)
*C09K 11/02* (2006.01)
*C09K 11/77* (2006.01)

(52) U.S. Cl.
CPC .............. *A61L 2/088* (2013.01); *C09K 11/02* (2013.01); *C09K 11/77064* (2021.01); *A61L 2103/05* (2026.01)

(58) Field of Classification Search
CPC ...... A61L 2/0076; A61L 2202/25; A61L 2/08; A61L 2/10; C09K 11/02; C09K 11/77064
See application file for complete search history.

(56) References Cited

U.S. PATENT DOCUMENTS 5,888,424 A 3/1999 Ebnesajjad et al.
2002/0124772 A1 9/2002 Egger et al.
2007/0257232 A1 11/2007 Tai et al.
2009/0085049 A1 4/2009 Kolodin et al.
2009/0085464 A1 4/2009 Oguma et al.
2009/0130169 A1 5/2009 Bernstein
2009/0230247 A1 9/2009 Harris
2010/0233368 A1 9/2010 Zhu et al.
(Continued)

FOREIGN PATENT DOCUMENTS

EP 3623447 A1 3/2020
JP 2000256591 A 9/2000
(Continued)

OTHER PUBLICATIONS

Haider, Ursula (PCT Authorized Officer), PCT Notification of Transmittal of the International Search Report and Written Opinion of the International Searching Authority issued Nov. 7, 2023 in International Application No. PCT/US2023/024855, 18 pages.
(Continued)

*Primary Examiner* — Brendan A Hensel
(74) *Attorney, Agent, or Firm* — MH2 Technology Law Group LLP

(57) ABSTRACT

Described herein are methods for disinfecting surfaces using a photon-emitting inorganic phosphor-doped substrate material. Methods for preparing the photon-emitting inorganic phosphor-doped substrate materials are additionally described.

19 Claims, 3 Drawing Sheets

Prepare inorganic phosphor dopant (100) 150

↓

Contact substrate material (101) with inorganic phosphor dopant (100) to prepare photon-emitting inorganic phosphor-doped substrate material 155

(56) References Cited

U.S. PATENT DOCUMENTS

| | | | |
|---|---|---|---|
| 2010/0295287 | A1 | 11/2010 | Reichert et al. |
| 2011/0038947 | A1 | 2/2011 | Maurer et al. |
| 2012/0119143 | A1 | 5/2012 | Jia et al. |
| 2012/0288972 | A1 | 11/2012 | McKean |
| 2014/0151607 | A1 | 6/2014 | Lowenthal et al. |
| 2016/0312052 | A1 | 10/2016 | Cong et al. |
| 2018/0194996 | A1 | 7/2018 | Frischeisen |
| 2019/0106583 | A1 | 4/2019 | Johansson et al. |
| 2020/0354596 | A1 | 11/2020 | Aoyama et al. |
| 2020/0377748 | A1 | 12/2020 | Aoyama et al. |
| 2021/0061929 | A1 | 3/2021 | Kobayashi et al. |
| 2023/0407121 | A1 | 12/2023 | Harris et al. |
| 2023/0407168 | A1 | 12/2023 | Harris |

FOREIGN PATENT DOCUMENTS

| | | | | |
|---|---|---|---|---|
| JP | 2004075888 | A | 3/2004 | |
| WO | 2007118813 | A1 | 10/2007 | |
| WO | 2009/064845 | A3 | 5/2009 | |
| WO | WO-2009064845 | A2 * | 5/2009 | ......... C09K 11/7777 |
| WO | 2012151765 | A1 | 11/2012 | |
| WO | 2017077446 | A1 | 5/2017 | |
| WO | 2017182638 | A1 | 10/2017 | |
| WO | 2018/153437 | A1 | 8/2018 | |
| WO | 2021/257688 | A1 | 12/2021 | |

OTHER PUBLICATIONS

Lehnert, Andreas (ISA Authorized Officer), PCT Notification of Transmittal of the International Search Report and the Written Opinion of the International Searching Authority, or the Declaration, issued Sep. 8, 2023 in related International Application No. PCT/US2023/024852, 10 pages.

Cameron, Lorraine (ISA Authorized Officer), PCT Notification of Transmittal of the International Search Report and the Written Opinion of the International Searching Authority, or the Declaration, issued Sep. 14, 2023 in related International Application No. PCT/US2023/024849, 12 pages.

* cited by examiner

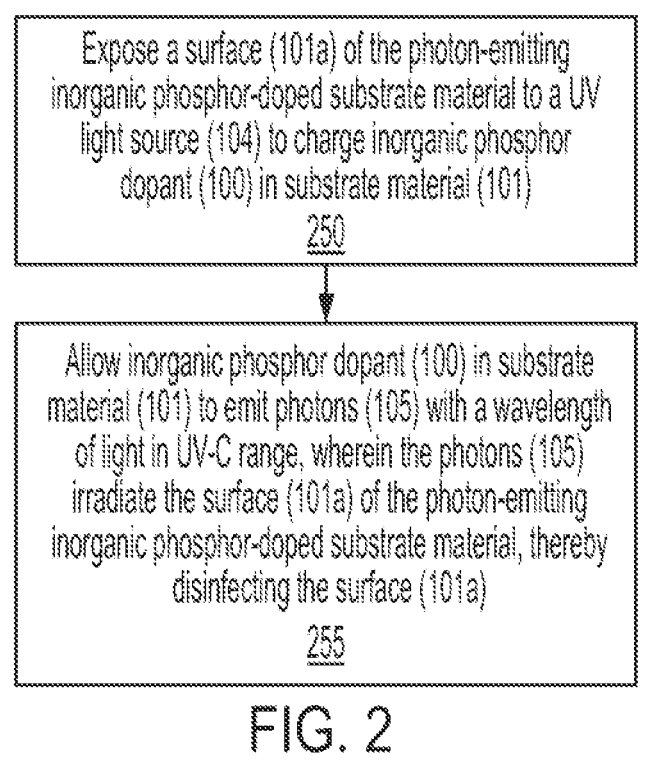

Expose a surface (101a) of the photon-emitting inorganic phosphor-doped substrate material to a UV light source (104) to charge inorganic phosphor dopant (100) in substrate material (101)
250

Allow inorganic phosphor dopant (100) in substrate material (101) to emit photons (105) with a wavelength of light in UV-C range, wherein the photons (105) irradiate the surface (101a) of the photon-emitting inorganic phosphor-doped substrate material, thereby disinfecting the surface (101a)
255

FIG. 2

SURFACE DISINFECTION WITH $PR^{3+}$DOPED INORGANIC PHOSPHORS

CROSS-REFERENCE TO RELATED APPLICATIONS

This application claims priority to U.S. Provisional Patent Application No. 63/366,576, filed on Jun. 17, 2022, the contents of which is hereby incorporated by reference in its entirety.

FIELD

The presently disclosed subject matter relates generally to methods for disinfecting surfaces by harnessing the luminescent properties of rare earth phosphors.

BACKGROUND

Phosphor materials have the properties of emitting ultraviolet, visible, and infrared light by action of external exciting means such as irradiation of electromagnetic waves (e.g., electron beams, X-rays, ultraviolet rays, visible light, etc.) or application of an electric field, and therefore are used in a large number of photoelectric transducers or photoelectric conversion devices. Examples of such devices are light-emitting devices, including white light-emitting diodes, fluorescent lamps, electron beam tubes, plasma display panels, inorganic electroluminescent displays, and scintillators. Inorganic phosphors, in particular, have been extensively explored to meet the demand of low voltage stimulated lighting sources owing to increased global energy consumption. Due to their environmental friendliness, advantages of long lifetime, lower energy consumption, reliability, and high luminous efficiency, modern white light-emitting diodes (WLEDs) have replaced less effective incandescent and mercury-enclosing conventional fluorescent lighting sources.

The lanthanides are often used as phosphors for luminescence applications. For example, praseodymium's shielded f-orbitals allow for long excited state lifetimes and high luminescence yields. Indeed, $Pr^{3+}$ is often a dopant ion for use in red, blue, green, and ultraviolet phosphors.

BRIEF SUMMARY

In one aspect, the presently disclosed subject matter is directed to a method for disinfecting a surface, comprising: exposing a surface of a substrate material comprising an inorganic phosphor dopant to a UV light source; wherein the exposing causes the inorganic phosphor dopant in the substrate material to emit photons; and wherein the photons irradiate the surface, thereby disinfecting the surface.

In another aspect, the presently disclosed subject matter is directed to a photon-emitting inorganic phosphor-doped substrate material, comprising: a substrate material comprising an inorganic phosphor dopant, wherein the inorganic phosphor dopant in the substrate material is capable of emitting photons upon exposure of a surface of the photon-emitting inorganic phosphor-doped substrate material to a UV light source.

In another aspect, the presently disclosed subject matter is directed to a method for preparing a photon-emitting material for surface disinfection, comprising: contacting a substrate material with an inorganic phosphor dopant to prepare an inorganic phosphor-doped substrate material, wherein the inorganic phosphor dopant in the inorganic phosphor-doped substrate material is capable of emitting photons upon exposure of a surface of the inorganic phosphor-doped substrate material to a UV light source.

These and other aspects are described fully herein.

BRIEF DESCRIPTION OF THE DRAWINGS

FIG. 2 shows a process for disinfecting a surface according to methods described herein.

DETAILED DESCRIPTION

The subject matter described herein relates to methods for disinfecting surfaces by harnessing the luminescent properties of inorganic phosphor dopant materials. The methods described herein offer several advantages over those of the art. Indeed, art methods for disinfecting surfaces include application of expensive and heavy ultraviolet light sources. Extended exposure to these light sources can affect the substrate surface. Long exposure times to pulsing UV light are conventionally required for high touch areas. Other disinfection methods of the art include wiping the surface with a disinfection solution that typically loses effectiveness over a short period of time. Further, exposure to such chemicals can have unintended effects on the substrate surface.

As described herein, incorporating inorganic phosphors into a substrate material provides an emitting surface of UV-C light (200 nm to 280 nm) that can be used to disinfect the substrate surface over an extended period of time. After exposing the phosphor-doped substrate surface to a UV excitation source, the surface emits photons for a tunable period of time after the excitation light has been removed. The phosphors in the substrate absorb UV light directly. The phosphors then emit radiant energy, which disinfects the substrate surface. In this regard, the disinfection comes from the substrate surface, itself. Furthermore, the disinfection methods described herein are durable in operation because the inorganic phosphors are incorporated homogeneously into the surface material, which minimizes degradation by wear or exposure to surface chemicals. The disinfection methods described herein can significantly reduce the time required to disinfect surfaces using conventional methods.

UV-C light is weak at the Earth's surface because the ozone layer of the atmosphere blocks it. Many disinfection methods use short-wavelength ultraviolet (ultraviolet C or UV-C) light to kill or inactivate microorganisms by destroying nucleic acids and disrupting their DNA, leaving them unable to perform vital cellular functions. The inorganic phosphors in the phosphor-doped substrate materials described herein emit such germicidal UV-C light, which works to disinfect the substrate surface.

Figure 3A:
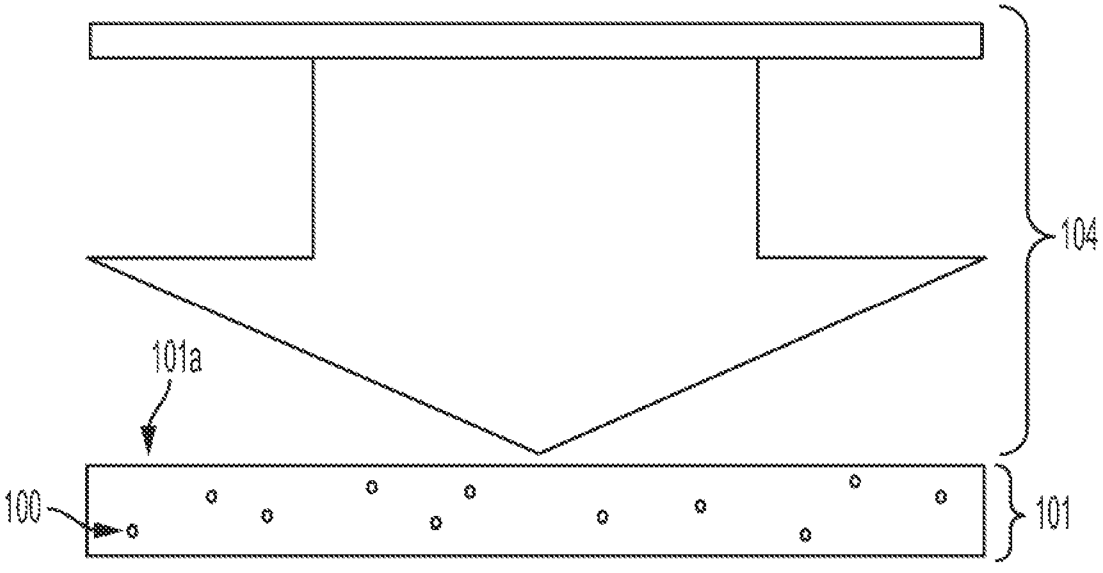
FIG. 3A shows a schematic of a process for charging an inorganic phosphor dopant in a substrate material in accordance with the disinfection methods described herein.
Figure 3B:
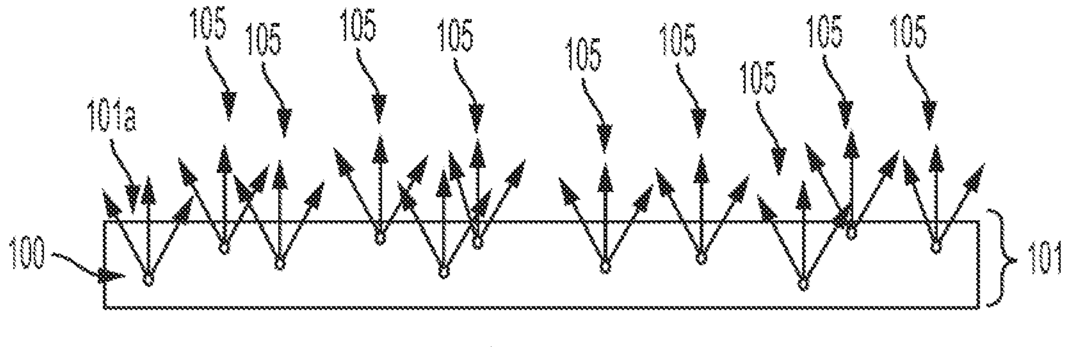
FIG. 3B shows a schematic of a process for disinfecting the surface of a substrate material in accordance with the methods described herein.

FIGS. 3A and 3B show schematics for charging an inorganic phosphor dopant in a substrate material and for disinfecting the surface of a substrate material, respectively, in accordance with the methods described herein. Briefly, in FIG. 3A, a surface (101*a*) of a substrate material (101) comprising an inorganic phosphor dopant (100) is exposed to a UV light source to charge the inorganic phosphor dopant (100). As shown in FIG. 3B, after charging the inorganic phosphor dopant (100) in the substrate material (101), the UV light from FIG. 3A is removed and the inorganic phosphor dopant (100) emits photons (105) having a wavelength of light in the UV-C range, wherein the photons (105) irradiate the surface (101*a*) of the substrate material (101), thereby disinfecting the surface (101*a*).

The presently disclosed subject matter will now be described more fully hereinafter. However, many modifications and other examples of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to specific examples disclosed and that modifications and other examples are intended to be included within the scope of the appended claims. In other words, the subject matter described herein covers all alternatives, modifications, and equivalents. Unless otherwise defined, all technical and scientific terms used herein have the same meaning as commonly understood by one of ordinary skill in this field. All publications, patent applications, patents, and other references mentioned herein are incorporated by reference in their entirety. In the event that one or more of the incorporated literatures, patents, and similar materials differs from or contradicts this application, including but not limited to defined terms, term usage, described techniques, or the like, this application controls.

I. Definitions

As used herein, "and/or" refers to and encompasses any and all possible combinations of one or more of the associated listed items, as well as the lack of combinations when interpreted in the alternative ("or").

The terms "approximately", "about", "essentially", and "substantially" as used herein represent an amount close to the stated amount that still performs a desired function or achieves a desired result. For example, in some examples, as the context may dictate, the terms "approximately", "about", and "substantially" may refer to an amount that is within less than or equal to 10% of the stated amount. The term "generally" as used herein represents a value, amount, or characteristic that predominantly includes or tends toward a particular value, amount, or characteristic.

As used herein, conditional language, such as, among others, "can", "could", "might", "may", "e.g.", and the like, unless specifically stated otherwise or otherwise understood within the context as used, is generally intended to convey that certain examples include, while other examples do not include, certain features, elements and/or steps. Thus, such conditional language is not generally intended to imply that features, elements and/or steps are in any way required for one or more examples or that one or more examples necessarily include logic for deciding, with or without author input or prompting, whether these features, elements and/or steps are included or are to be performed in any particular example. The terms "comprising", "including", "having", and the like are synonymous and are used inclusively, in an open-ended fashion, and do not exclude additional elements, features, acts, operations, and so forth. The terms, "consisting of", "consist of", and "consists of", respectively, and the like are synonymous and used in a close-ended fashion, and exclude additional elements, features, acts, operations, and so forth. The terms "consisting essentially of", "consist essentially of", "consists essentially of" and the like are synonymous and semi-closed terms that indicate an item in the claim is limited to the components specified in the claim and those that do not materially affect the basic and novel characteristics of the claim. Additionally, the term "or" is used in its inclusive sense (and not in its exclusive sense) so that when used, for example, to connect a list of elements, the term "or" means one, some, or all of the elements in the list.

As used herein, "contacting" refers to contacting a substrate material (101) with an inorganic phosphor dopant (100) to prepare a photon-emitting inorganic phosphor-doped substrate material. As used herein, an inorganic phosphor dopant (100) refers to a rare earth ion (107) or transition metal-containing metal oxide (106) or metal fluoride (108). The substrate material (101) acts as a host material, wherein the inorganic phosphor dopant (100) is incorporated into the host material through, for example, application of heat and/or pressure. In certain examples, the photon-emitting inorganic phosphor-doped substrate material comprises about 0.05% to about 10% weight or about 0.01 to about 5% weight of the inorganic phosphor dopant. In certain other examples, the photon-emitting inorganic phosphor-doped substrate material comprises about 0.05% to about 0.15%, about 0.10% to about 0.25%, about 0.15% to about 3%, about 0.25% to about 4%, about 1% to about 5%, about 1.5% to about 3.5%, about 2.5% to about 4%, about 0.50% to about 4.5%, about 4 to about 5%, about 5% to about 10%, about 3% to about 7%, about 4% to about 8%, about 6% to about 9%, or about 7% to about 10% weight of inorganic phosphor dopant.

As used herein, "photo-oxidation" refers to degradation of a polymer surface due to the combined action of light and oxygen. Photo-oxidation causes the polymer chains to break, resulting in the material becoming increasingly brittle.

II. Method for Disinfecting a Surface

In certain examples, such as depicted in FIG. 2, the subject matter described herein is directed to a method for disinfecting a surface (101*a*), comprising:

exposing a surface (101*a*) of a substrate material (101) comprising an inorganic phosphor dopant (100) to a UV light source (104) to charge the inorganic phosphor dopant in the substrate material (101) in Step 250 of FIG. 2;

wherein the exposing causes the inorganic phosphor dopant (100) in the substrate material (101) to emit photons (105) with a wavelength of light in the UV-C range, wherein the photons (105) irradiate the surface (101*a*) of the photon-emitting inorganic phosphor-doped substrate material, thereby disinfecting the surface (101*a*) in Step 255 of FIG. 2.

When a phosphor is exposed to radiation, the orbital electrons in its molecules are excited to a higher energy level; when they return to their former level they emit the energy as light of a certain color. Indeed, the scintillation process in inorganic materials is due to the electronic band structure found in the crystals. An incoming particle can excite an electron from the valence band to either the conduction band or the exciton band (located just below the conduction band and separated from the valence band by an energy gap). This leaves an associated hole behind, in the valence band. Impurities create electronic levels in the forbidden gap. The excitons are loosely bound electron-hole pairs that diffuse through the crystal lattice until they are captured as a whole by impurity centers. The latter then rapidly de-excite by emitting scintillation light (i.e. a photon). The wavelength emitted is dependent on the atom itself and on the surrounding crystal structure.

In certain examples, the UV light source (104) used to excite (charge) the orbital electrons of the inorganic phosphor dopant has a wavelength between about 160 nm and 320 nm. In other examples, the UV light source (104) has a wavelength between about 160 nm and 260 nm, about 160 nm and 200 nm, about 180 nm and 240 nm, about 200 nm and 250 nm, about 210 nm and 250 nm, about 225 nm and 260 nm, about 230 nm and 250 nm, or about 190 nm and 260 nm. In certain other examples, the UV light source has a wavelength of about 222 nm, 254 nm, or 275 nm.

Nonlimiting examples of UV light sources (104) include, for example, a black light, a short-wave ultraviolet lamp, an incandescent lamp, a gas-discharge lamp, an ultraviolet LED, a deuterium lamp, a pulsed Xenon light, and an ultraviolet laser. In an example, the UV light source (104) is a pulsed Xenon-ultraviolet device, which can be in the form of a handheld wand. The ultraviolet light emitted from a pulsed Xenon device allows for efficient charging of the inorganic phosphor dopant (100) in the substrate material (101) and can disinfect a surface (101*a*) by hovering the Xenon-ultraviolet wand about 1 to 5 inches over the surface (101*a*). In another example, the UV light source (104) is a deuterium lamp, which has a range of light from about 185 nm to about 400 nm.

Other excitation energy sources, in addition to UV light, may be used in the methods described herein. Personal Protection Equipment (PPE) may be required for operating such energy sources.

In certain examples of the above method, the inorganic phosphor dopant (100) in the substrate material (101) emits photons (105) with a wavelength of light between about 200 nm and 280 nm. In other examples, the inorganic phosphor dopant (100) in the substrate material (101) emits photons (105) with a wavelength of light between about 200 nm and 270 nm, about 200 nm and 250 nm, about 225 nm and 250 nm, about 200 nm and 225 nm, about 200 nm and 275 nm, or about 225 nm and 275 nm. The emission wavelength of the inorganic phosphor dopant (100) can be tuned by varying the excitation wavelength of the phosphor. In preferred examples, the inorganic phosphor dopant emits UV-C light, having a wavelength of about 200 to 280 nm.

In certain examples, the inorganic phosphor dopant (100) is a metal oxide (106) or metal fluoride (108) comprising a rare earth ion (107) or transition metal ion. In certain examples, the rare earth ion (107) or transition metal ion is referred to as an "activator ion." As used herein, the "activator ion" is the ion added as a dopant to the crystal structure. The activator ions are surrounded by host-crystal ions and form luminescing centers where the excitation-emission process of the phosphor occurs. The wavelength emitted by the activator ion is influenced by the ion itself, its electronic configuration, and its surrounding crystal structure.

Although the activator ions have intrinsic characteristics that contribute to the optical properties of phosphors, the electronic energy levels of an activator ion in a crystal differ from those of the free ion. The separation of the energy levels can give rise to emission of light from UV across visible wavelengths, depending on the properties of the host crystal. The local geometry around the activator ion affects the spectroscopic behavior of activator ions, in particular, lanthanide ions, incorporated in the host matrix. Certain effects in the crystal lattice, such as ligand field splitting, and centroid shift, can affect energy gaps between f and d orbitals of the activator ion, thereby influencing the luminescence properties of such materials (Lin, Y C., et al. *Top Curr Chem* (*Z*) 374, 21 (2016)).

In certain examples, the inorganic phosphor dopant (100) is a metal oxide (106) comprising a rare earth ion (107). In certain examples, the rare earth ion (107) is a lanthanide ion. In certain examples, the rare earth ion (107) is selected from the group consisting of $Tm^{3+}$, $Pr^{3+}$, $Ho^{3+}$, $Er^{3+}$, $Sm^{3+}$, $Nd^{3+}$, $Yb^{3+}$, $Eu^{3+}$, $Eu^{2+}$, $Gd^{3+}$, $Ce^{3+}$, $Ce^{2+}$, $Tb^{3+}$, $Tb^{4+}$, $Dy^{3+}$, $Yb^{3+}$, and $Lu^{3+}$, or a combination thereof. In certain examples, the inorganic phosphor dopant (100) is a metal oxide (106) comprising a rare earth ion (107) selected from the group consisting of $Pr^{3+}$, $Ce^{3+}$, $Eu^{3+}$, $Eu^{2+}$, $Gd^{3+}$, $Tb^{3+}$, and $Dy^{3+}$, or a mixture thereof. In certain examples, the rare earth ion (107) is $Pr^{3+}$.

The UV-C emission of $Pr^{3+}$-activated UV-C phosphors is dominated by broad, parity allowed $Pr^{3+}$ $4f^15d^1 \rightarrow 4f^2$ interconfigurational transitions. To ensure the occurrence of $Pr^3+4f^15d^1 \rightarrow 4f^2$ transitions in the UV-C in a solid, two general conditions are required: a small Stokes shift of less than about 3000 $cm^{-1}$ (0.37 eV) and an appropriate energy location of the first (lowest energy) $Pr^{3+}$ $4f^2 \rightarrow 4f^15d^1$ excitation transition, which are associated with the compositions and crystal structures of the host lattice. Under these conditions, the nonradiative relaxation of the $Pr^3+4f^15d^1$ level to the lower 4f ($^3P_J$, $^1I_6$, $^1D_2$) levels is minimized; otherwise, crossing of the $4f^15d^1$ level with the lower 4f levels will occur and, as a result, sharp line $4f^2 \rightarrow 4f^2$ intraconfigurational emission transmission for visible and infrared-light emission will dominate (Wang, X., et al. *Nat Commun* 11, 2040 (2020)).

In certain examples of the inorganic phosphor dopant (100), the metal oxide (106) (host lattice) is selected from the group consisting of silicates, phosphates, borates, oxides, oxynitrides, oxysulfides, and aluminates, or combinations thereof. Such metal oxides (106) are ceramic materials and thus exhibit several advantages, including chemical, thermal, and photochemical stability. In certain examples, the silicate is selected from the group consisting of melilite, cyclosilicate, silicate garnet, oxyorthosilicate, and orthosilicate. Nonlimiting examples of silicates include $Sr_2MgSi_2O_7$, $Ca_2Al_2SiO_7$, $SrAl_2O_4$, $MgSiO_3$, $SrSiO_3$, $CdSiO_3$, $Ba_2SiO_4$, $BaMg_2Si_2O_7$, $Ca_2MgSi_2O_7$, $Sr_{0.5}Ca_{1.5}MgSi_2O_7$, $(Ca,Sr)_2MgSi_2O_7$, $Sr_3MgSi_2O_8$, $Sr_2MgSi_2O_7$, $Ca_{0.5}Sr_{1.5}Al_2SiO_7$, $Sr_3Al_{10}SiO_{20}$, and $Y_2SiO_5$. Nonlimiting examples of borates include $YBO_3$ and $CaAl_2B_2O_7$. Nonlimiting examples of oxynitrides include $MSi_2O_2N_2$, wherein M=Ba, Sr, or Ca. Nonlimiting examples of phosphates include $YPO_4$ and $Zn_3(PO_4)_2$. Nonlimiting examples of oxides include CaO, SrO, BaO, $Y_3Ga_5O_{12}$, $NaGdGeO_4$, $Cd_3Al_2Ge_3O_{12}$, $CaTiO_3$, $Ca_{0.8}Zn_{0.2}TiO_3$, and $Ca_2Zn_4Ti_{15}O_{36}$. Nonlimiting examples of oxysulfides include $Y_2O_2S$, $Gd_2O_2S$, and $Sr_5Al_2O_7S$. Nonlimiting examples of aluminates include $MgAl_2O_4$, $CaAl_2O_4$, $SrAl_2O_4$, and $Sr_4Al_{14}O_{25}$.

In certain examples of the inorganic phosphor dopant (100), the metal oxide (106) is $Ca_2Al_2SiO_7$ doped with $Pr^{3+}$($Ca_2Al_2SiO_7$:$Pr^{3+}$). $Ca_2Al_2SiO_7$ is characterized by the melilite structure, in which $Ca^{2+}$ ions are sandwiched between layers of $AlO_4$ and $SiO_4$ tetrahedrons alternating along the c axis and are eightfold coordinated. Each $Ca^{2+}$ ion is bonded to four nearest neighbor $O^{2-}$ ligand ions in both the $AlO_4$ layer and the $SiO_4$ layer, and therefore the four $Ca^{2+}$ complexes in a unit cell are structurally equivalent. In $Ca_2Al_2SiO_7$:$Pr^{3+}$, trivalent $Pr^{3+}$ ions (1.126 Å) substitute for smaller, divalent $Ca^{2+}$ ions (1.12 Å). As such, the doped $Pr^{3+}$ ions are eightfold coordinated. Such highly coordinated, smaller, and charge-imbalanced cation sites can create a suitably strong crystal field for $Pr^{3+}$ ions, by which a small Stokes shift and therefore an efficient $Pr^{3+}$ $4f^15d^1 \rightarrow 4f^2$ interconfigurational transition for UV-C emission is likely to occur. Moreover, without wishing to be bound by theory, the cation size mismatch and charge imbalance are expected to create more effective energy traps (e.g. oxygen vacancies) around $Pr^{3+}$ ions, which help generate effective persistent phosphors (Wang, X., et al. *Nat Commun* 11, 2040 (2020)).

In certain examples of the inorganic phosphor dopant (100), the metal fluoride (108) (host lattice) is selected from the group consisting of $Cs_2NaYF_6$, $NaCeF_4$, $NaYF_4$, and $NaGd_4$. Such metal fluoride hosts are often characterized as having a large bandgap, structural defects that are likely to act as electron traps, and anionic defects, which make them useful for inorganic phosphors. In certain examples, the inorganic phosphor dopant (100) is $Cs_2NaYF_6$ doped with $Pr^{3+}$ ($Cs_2NaYF_6$:$Pr^{3+}$). In an example, the $Pr^{3+}$ substitutes the yttrium ion site in $Cs_2NaYF_6$ in an amount from about 0.3% to about 10%. In other examples, the $Pr^{3+}$ substitutes the yttrium ion site in $Cs_2NaYF_6$ in an amount from about 1% to 5%, 1.5% to 4.5%, 2.5% to 5%, 2% to 7%, 3% to 8%, or 4% to 9%.

In certain examples, the substrate material (101) comprises one or more synthetic polymers. Synthetic polymers are efficient, durable, and inexpensive materials and can be readily modified by heating and/or pressure techniques to incorporate the inorganic phosphors described herein. In certain examples, the substrate material (101) comprises a material selected from the group consisting of optionally fluorinated thermoplastics, thermosetting resins, and electronegative resins. In certain other examples, the substrate material (101) comprises a material selected from the group consisting of tetrafluoroethylene, polyvinyl fluoride, polyurethane, polyester, epoxy, phenolic, vinyl ester, polyamide, polyamide-imide, polyether imide, polyvinylchloride, polyether ketone, polycarbonate, polyphenylsulphone, polymethylmethacrylate, polyacrylate, and benzoxazine, or a combination thereof. In particular, fluorine is known to strongly resist photo-oxidation because of its high electronegativity and desire to accept an electron. As such, in certain examples, fluorinated synthetic polymers, such as tetrafluoroethylene or polyvinyl fluoride, are useful for the synthetic polymers in the methods described herein. Additionally, thermosetting polymers are generally known to have a higher degree of cross linking compared to other types of polymers, which makes them further resistant to photo-oxidation.

The substrate material (101) comprising one or more synthetic polymers can be applied in virtually any environment for surface disinfection. In certain examples, the substrate material (101) comprising one or more synthetic polymers is located in an airplane, a hospital, a gym, a school, or other areas where there is significant risk of fomite transfer.

In certain examples of the above method, the surface (101*a*) is an interior of an airplane. In certain other examples of the above method, the surface (101*a*) is located in a hospital, a gym, or a school. In another example of the above method, the surface resides where there is significant risk of fomite transfer.

In some examples, materials can be used to reduce the effect of shadowing of surface areas and thereby assist in disinfecting surfaces that do not receive incident UV light exposure. For example, inorganic phosphor dopants (100) can be incorporated into polyvinyl fluoride (PVF) used in decorative laminates to increase the surface area of the substrate material (101) capable of emitting photons.

In examples of the above method for disinfecting a surface, the exposing the substrate material (101) comprising the inorganic phosphor dopant (100) to a UV light source (104) is for a time sufficient to charge the inorganic phosphor dopant (100) in the substrate material (101). In certain examples, the time sufficient to charge the inorganic phosphor dopant (100) in the substrate material (101) is for about one second to two seconds, one second to thirty seconds, one second to twenty-five seconds, one second to twenty seconds, one second to fifteen seconds, one second to ten seconds, one second to five seconds, two seconds to five seconds, three seconds to fifteen seconds, five seconds to ten seconds, one minute, two minutes, three minutes, four minutes, five minutes, ten minutes, fifteen minutes, twenty minutes, thirty minutes, forty-five minutes, one hour, two hours, three hours, five hours, seven hours, ten hours, fifteen hours, twenty hours, or twenty-four hours. The amount of time sufficient to charge the inorganic phosphor dopant (100) in the substrate material will vary, depending on the wavelength of the UV light from the UV light source (104) and the inorganic phosphor dopant (100), itself.

In examples of the above method for disinfecting a surface, the inorganic phosphor dopant (100) in the substrate material (101) emits photons (105) for about two minutes, three minutes, four minutes, five minutes, six minutes, seven minutes, eight minutes, nine minutes, ten minutes, eleven minutes, twelve minutes, thirteen minutes, fourteen minutes, fifteen minutes, sixteen minutes, seventeen minutes, eighteen minutes, nineteen minutes, twenty minutes, twenty-five minutes, thirty minutes, forty-five minutes, or sixty minutes. The amount of time during which the inorganic phosphor dopant (100) emits photons (105) can be tuned, for example, by modifying the length of time for charging the inorganic phosphor dopant (100). The duration of emission can also be tuned, depending on the desired application. For example, if the surface to be disinfected is located in an airplane, a suitable maximum emission time is about ten minutes, fifteen minutes, twenty minutes, twenty-five minutes, or thirty minutes, such that the disinfection process can proceed in between flights. In certain other examples, longer emission times may correlate with greater levels of disinfection. For example, if the surface to be disinfected is located in a hospital or healthcare facility, emission times could range between about thirty minutes and sixty minutes, as a higher level of disinfection may be desired in this type of setting.

One or more dopant ions can be used to tailor the emissivity to longer or shorter wavelengths, as well as modify the emission intensity. For example, $SrAl_2O_4$ can be doped with $Eu^{2+}$, yielding a phosphor that emits at 520 nm. However, $SrAl_2O_4$ can also be co-doped with $Eu^{2+}$ and $Dy^{3+}$, and works to considerably enhance the persistent luminescent intensity. At room temperature, the afterglow of $SrAl_2O_4$:$Eu^{2+}$, $Dy^{3+}$ lasts for several hours, which is the result of the gradual, thermally assisted release of trapped charges in the phosphor. This long afterglow is in contrast to the duration of only a few minutes for the variant without co-dopant (Xingdong, L., et al. *J. Wuhan Univ. Technol.—Mat. Sci. Edit.* 23, 652-657 (2008)). Further, the materials can be stabilized with inorganic phosphor dopants (100) having energy traps, which can be filled during excitation. The energy traps can be tailored by adjusting the required depth of penetration of UV energy to adjust the decay time needed to decontaminate a surface over time.

As the light emitted by the inorganic phosphor dopant (100) in the photon-emitting inorganic phosphor-doped substrate material leaves the substrate, it isotropically irradiates the substrate surface (101*a*), thereby disinfecting the surface (101*a*). Isotropic irradiation refers to radiation from a point source, radiating uniformly in all directions, with the same intensity, regardless of the direction of the measurement. The light emitted by the inorganic phosphor dopants (100) is short wavelength ultraviolet (ultraviolet C or UV-C) light, having a range between 200 nm to 280 nm or 225 nm to 250 nm, which is known to be germicidal.

In certain examples of the method for disinfecting a surface, the substrate material (101) comprises tetrafluoroethylene or polyvinyl fluoride; the UV light source (104) has a wavelength of about 160 to 260 nm; the inorganic phosphor dopant (100) is a silicate comprising $Pr^{3+}$; and wherein the inorganic phosphor dopant (100) emits photons (105) having a wavelength of light of about 265 nm.

III. Photon-Emitting Inorganic Phosphor-Doped Substrate Material

In certain examples, the subject matter described herein is directed to a photon-emitting inorganic phosphor-doped substrate material, comprising:

- a substrate material (101) comprising an inorganic phosphor dopant (100), wherein the inorganic phosphor dopant (100) in the substrate material (101) is capable of emitting photons (105) upon exposure of a surface of the photon-emitting inorganic phosphor-doped substrate material to a UV light source (104).

In certain examples of the photon-emitting inorganic phosphor-doped substrate material, the substrate material comprises one or more synthetic polymers. In certain examples, the substrate material comprises a material selected from the group consisting of optionally fluorinated thermoplastics, thermosetting resins, and electronegative resins. In certain examples, the substrate material comprises a material selected from the group consisting of tetrafluoroethylene, polyvinyl fluoride, polyurethane, polyester, epoxy, phenolic, vinyl ester, polyamide, polyamide-imide, polyether imide, polyvinylchloride, polyether ketone ketone, polycarbonate, polyphenylsulphone, polymethylmethacrylate, polyacrylate, and benzoxazine. In certain examples of the photon-emitting inorganic phosphor-doped substrate material, the substrate material is an airplane interior.

In certain examples of the photon-emitting inorganic phosphor-doped substrate material, the inorganic phosphor dopant (100) is a metal oxide (106) or a metal fluoride (108) comprising a rare earth ion (107) or transition metal ion. In certain examples of the photon-emitting inorganic phosphor-doped substrate material, the inorganic phosphor dopant (100) is a metal oxide (106). In certain examples, the rare earth ion (107) is a lanthanide ion. In certain examples, the rare earth ion (107) is selected from the group consisting of $Tm^{3+}$, $Pr^{3+}$, $Ho^{3+}$, $Er^{3+}$, $Sm^{3+}$, $Nd^{3+}$, $Yb^{3+}$, $Eu^{3+}$, $Eu^{2+}$, $Gd^{3+}$, $Ce^{3+}$, $Ce^{2+}$, $Tb^{3+}$, $Tb^{4+}$, $Dy^{3+}$, $Yb^{3+}$, and $Lu^{3+}$, or a combination thereof. In certain examples, the inorganic phosphor dopant (100) is a metal oxide (106) comprising a rare earth ion (107) selected from the group consisting of $Pr^{3+}$, $Ce^{3+}$, $Eu^{3+}$, $Eu^{2+}$, $Gd^{3+}$, $Tb^{3+}$, and $Dy^{3+}$, or a mixture thereof. In certain examples, the rare earth ion (107) is $Pr^{3+}$.

In certain examples of the inorganic phosphor dopant (100), wherein the inorganic phosphor dopant (100) is a metal oxide (106), the metal oxide (106) is selected from the group consisting of silicates, phosphates, borates, oxides, oxynitrides, oxysulfides, and aluminates, or combinations thereof. In certain examples, the silicate is selected from the group consisting of melilite, cyclosilicate, silicate garnet, oxyorthosilicate, and orthosilicate. Nonlimiting examples of silicates include $Sr_2MgSi_2O_7$, $Ca_2Al_2SiO_7$, $SrAl_2O_4$, $MgSiO_3$, $SrSiO_3$, $CdSiO_3$, $Ba_2SiO_4$, $BaMg_2Si_2O_7$, $Ca_2MgSi_2O_7$, $Sr_{0.5}Ca_{1.5}MgSi_2O_7$, $(Ca,Sr)_2MgSi_2O_7$, $Sr_3MgSi_2O_8$, $Sr_2MgSi_2O_7$, $Ca_{0.5}Sr_{1.5}Al_2SiO_7$, $Sr_3Al_{10}SiO_{20}$, and $Y_2SiO_5$. Nonlimiting examples of borates include $YBO_3$ and $CaAl_2B_2O_7$. Nonlimiting examples of oxynitrides include $MSi_2O_2N_2$, wherein M=Ba, Sr, or Ca. Nonlimiting examples of phosphates include $YPO_4$ and $Zn_3(PO_4)_2$. Nonlimiting examples of oxides include CaO, SrO, BaO, $Y_3Ga_5O_{12}$, $NaGdGeO_4$, $Cd_3Al_2Ge_3O_{12}$, $CaTiO_3$, $Ca_{0.8}Zn_{0.2}TiO_3$, and $Ca_2Zn_4Ti_{15}O_{36}$. Nonlimiting examples of oxysulfides include $Y_2O_2S$, $Gd_2O_2S$, and $Sr_5Al_2O_7S$. Nonlimiting examples of aluminates include $MgAl_2O_4$, $CaAl_2O_4$, $SrAl_2O_4$, and $Sr_4Al_{14}O_{25}$.

In certain examples of the inorganic phosphor dopant (100), the metal oxide (106) is $Ca_2Al_2SiO_7$ doped with $Pr^{3+}$.

In certain examples of the inorganic phosphor dopant (100), the metal fluoride (108) (host lattice) is selected from the group consisting of $Cs_2NaYF_6$, $NaCeF_4$, $NaYF_4$, and $NaGd_4$. Such metal fluoride hosts are often characterized as having a large bandgap, structural defects that are likely to act as electron traps, and anionic defects, which make them useful for inorganic phosphors. In certain examples, the inorganic phosphor dopant (100) is $Cs_2NaYF_6$ doped with $Pr^{3+}$ ($Cs_2NaYF_6$:$Pr^{3+}$). In an example, the $Pr^{3+}$ substitutes the yttrium ion site in $Cs_2NaYF_6$ in an amount from about 0.3% to about 10%. In other examples, the $Pr^{3+}$ substitutes the yttrium ion site in $Cs_2NaYF_6$ in an amount from about 1% to 5%, 1.5% to 4.5%, 2.5% to 5%, 2% to 7%, 3% to 8%, or 4% to 9%.

In certain examples of the photon-emitting inorganic phosphor-doped substrate material, the inorganic phosphor dopant (100) in the substrate material (101) is capable of emitting photons (105) with a wavelength of light between about 200 nm and 280 nm upon exposure of a surface (101*a*) of the photon-emitting inorganic phosphor-doped substrate material to a UV light source (104). In certain examples of the photon-emitting inorganic phosphor-doped substrate material, the inorganic phosphor dopant (100) in the substrate material (101) is capable of emitting photons (105) with a wavelength of light between about 200 nm and 270 nm, about 200 nm and 250 nm, about 225 nm and 250 nm, about 200 nm and 225 nm, about 200 nm and 275 nm, or about 225 nm and 275 nm.

IV. Methods for Preparing a Photon-emitting Material

Figure 1:
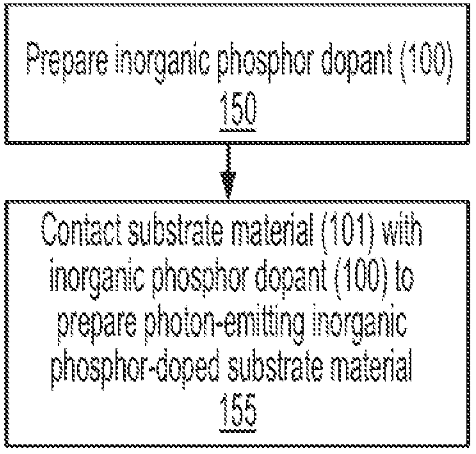
FIG. 1 shows a process for preparing a photon-emitting inorganic phosphor-doped substrate material described herein.

In certain examples, such as depicted in FIG. 1, the subject matter described herein is directed to a method for preparing a photon-emitting material for surface disinfection, comprising:

- preparing an inorganic phosphor dopant (100) in Step 150 of FIG. 1; and
- contacting a substrate material (101) with the inorganic phosphor dopant (100) to prepare a photon-emitting inorganic phosphor-doped substrate material in Step 155 of FIG. 1, wherein the inorganic phosphor dopant (100) in the photon-emitting inorganic phosphor-doped substrate material is capable of emitting photons (105) upon exposure of a surface (101*a*) of the photon-emitting inorganic phosphor-doped substrate material to a UV light source (104).

In certain examples of the method for preparing a photon-emitting material for surface disinfection, the inorganic phosphor dopant (100) in the photon-emitting inorganic phosphor-doped substrate material is capable of emitting photons (105) with a wavelength of light between about 200 nm and 280 nm. In certain examples of the method for preparing a photon-emitting material for surface disinfection, the inorganic phosphor dopant (100) in the photon-emitting inorganic phosphor-doped substrate material is capable of emitting photons (105) with a wavelength of light between about 200 nm and 270 nm, about 200 nm and 250 nm, about 225 nm and 250 nm, about 200 nm and 225 nm, about 200 nm and 275 nm, or about 225 nm and 275 nm.

In certain examples of the method for preparing a photon-emitting material for surface disinfection, the inorganic phosphor dopant (100) is a metal oxide (106) or a metal fluoride (108) comprising a rare earth ion (107) or transition metal ion. In certain examples of the method for preparing a photon-emitting material for surface disinfection, the inorganic phosphor dopant (100) is a metal oxide (106). In certain examples, the rare earth ion (107) is a lanthanide ion. In certain examples, the rare earth ion (107) is selected from the group consisting of $Tm^{3+}$, $Pr^{3+}$, $Ho^{3+}$, $Er^{3+}$, $Sm^{3+}$, $Nd^{3+}$, $Yb^{3+}$, $Eu^{3+}$, $Eu^{2+}$, $Gd^{3+}$, $Ce^{3+}$, $Ce^{2+}$, $Tb^{3+}$, $Tb^{4+}$, $Dy^{3+}$, $Yb^{3+}$, and $Lu^{3+}$, or a combination thereof. In certain examples, the inorganic phosphor dopant (100) is a metal oxide (106) comprising a rare earth ion (107) selected from the group consisting of $Pr^{3+}$, $Ce^{3+}$, $Eu^{3+}$, $Eu^{2+}$, $Gd^{3+}$, $Tb^{3+}$, and $Dy^{3+}$, or a mixture thereof. In certain examples, the rare earth ion (107) is $Pr^{3+}$.

In certain examples of the method for preparing a photon-emitting material for surface disinfection, the metal oxide (106) is selected from the group consisting of silicates, phosphates, borates, oxides, oxynitrides, oxysulfides, and aluminates, or combinations thereof. In certain examples, the silicate is selected from the group consisting of melilite, cyclosilicate, silicate garnet, oxyorthosilicate, and orthosilicate. Nonlimiting examples of silicates include $Sr_2MgSi_2O_7$, $Ca_2Al_2SiO_7$, $SrAl_2O_4$, $MgSiO_3$, $SrSiO_3$, $CdSiO_3$, $Ba_2SiO_4$, $BaMg_2Si_2O_7$, $Ca_2MgSi_2O_7$, $Sr_{0.5}Ca_{1.5}MgSi_2O_7$, $(Ca,Sr)_2MgSi_2O_7$, $Sr_3MgSi_2O_8$, $Sr_2MgSi_2O_7$, $Ca_{0.5}Sr_{1.5}Al_2SiO_7$, $Sr_3Al_{10}SiO_{20}$, and $Y_2SiO_5$. Nonlimiting examples of borates include $YBO_3$ and $CaAl_2B_2O_7$. Nonlimiting examples of oxynitrides include $MSi_2O_2N_2$, wherein M=Ba, Sr, or Ca. Nonlimiting examples of phosphates include $YPO_4$ and $Zn_3(PO_4)_2$. Nonlimiting examples of oxides include CaO, SrO, BaO, $Y_3Ga_5O_{12}$, $NaGdGeO_4$, $Cd_3Al_2Ge_3O_{12}$, $CaTiO_3$, $Ca_{0.8}Zn_{0.2}TiO_3$, and $Ca_2Zn_4Ti_{15}O_{36}$. Nonlimiting examples of oxysulfides include $Y_2O_2S$, $Gd_2O_2S$, and $Sr_5Al_2O_7S$. Nonlimiting examples of aluminates include $MgAl_2O_4$, $CaAl_2O_4$, $SrAl_2O_4$, and $Sr_4Al_{14}O_{25}$.

In certain examples of the inorganic phosphor dopant (100), the metal oxide (106) is $Ca_2Al_2SiO_7$ doped with $Pr^{3+}$.

In certain examples of the inorganic phosphor dopant (100), the metal fluoride (108) (host lattice) is selected from the group consisting of $Cs_2NaYF_6$, $NaCeF_4$, $NaYF_4$, and $NaGd_4$. Such metal fluoride hosts are often characterized as having a large bandgap, structural defects that are likely to act as electron traps, and anionic defects, which make them useful for inorganic phosphors. In certain examples, the inorganic phosphor dopant (100) is $Cs_2NaYF_6$ doped with $Pr^{3+}$($Cs_2NaYF_6$:$Pr^{3+}$). In an example, the $Pr^{3+}$ substitutes the yttrium ion site in $Cs_2NaYF_6$ in an amount from about 0.3% to about 10%. In other examples, the $Pr^{3+}$ substitutes the yttrium ion site in $Cs_2NaYF_6$ in an amount from about 1% to 5%, 1.5% to 4.5%, 2.5% to 5%, 2% to 7%, 3% to 8%, or 4% to 9%.

In certain examples of the method for preparing a photon-emitting material for surface disinfection, the substrate material (101) comprises one or more synthetic polymers. In certain examples, the substrate material (101) comprises a material selected from the group consisting of optionally fluorinated thermoplastics, thermosetting resins, and electronegative resins. In certain examples, the substrate material (101) comprises a material selected from the group consisting of tetrafluoroethylene, polyvinyl fluoride, polyurethane, polyester, epoxy, phenolic, vinyl ester, polyamide, polyamide-imide, polyether imide, polyvinylchloride, polyether ketone ketone, polycarbonate, polyphenylsulphone, polymethylmethacrylate, polyacrylate, and benzoxazine. As described in other examples herein, fluorinated polymers, in particular, strongly resist photo-oxidation.

In certain examples of the method for preparing a photon-emitting material for surface disinfection, the substrate material (101) comprises tetrafluoroethylene or polyvinyl fluoride and the inorganic phosphor dopant (100) is a silicate comprising $Pr^3$. In certain examples, the silicate is $Ca_2Al_2SiO_7$.

Methods for preparing inorganic phosphor dopants (100) are known in the art. See, for example, Broxtermann et al. *ECS Journal of Solid State Science and Technology,* 6 (4) R47-R52 (2017); and Poelman et al. *Journal of Applied Physics* 128, 240903 (2020). In examples, metal oxide (106) host materials and rare earth oxides are weighed out such that an amount of rare earth ion (107) is substituted or doped into the metal oxide lattice. The amount of ion to be added can be determined by calculating the proposed stoichiometry of the material and then weighing out appropriate amounts of starting materials using dimensional analysis. The metal oxide (106) powders are intimately ground up using a mortar and pestle in order to maximize contact between the particles in the mixture. Once placed in a suitable crucible (often alumina), the mixture is heated in a tube or muffle furnace up to a temperature, sufficient to induce a solid state reaction, but below the melting temperature of the final compound. From a temperature around 200-300° C. below this melting temperature, there is a strong increase in the grain size of the final compound. This heating process is called sintering, which typically leads to very a dense and strongly agglomerated material. This material is not directly applicable as a phosphor. Therefore, post-synthesis grinding—manually or using a ball mill—is often required.

Ball milling is a mechanical method whereby particles are reduced in size by mechanical impact and friction. Typically, powders are placed in a grinding jar, together with a number of hard grinding balls (often $Al_2O_3$ or $ZrO_2$) and a solvent so that a slurry is obtained. The grinding jar is then moved in order to achieve maximum friction. Similar to the case of manual grinding using a mortar and pestle, the effect of the process is highly dependent on the size and hardness of the starting material.

For the solid-state synthesis described above, the atmosphere used for heating can vary depending on the host material. In the case of oxides, air can usually be applied. However, some dopants, notably europium, can be oxidized in an oxygen lattice while heating in oxygen, leading to the formation of fully oxidized $Eu^{3+}$ dopants. If $Eu^{2+}$ is the preferred valence state of this dopant, then it can be necessary to perform an additional thermal treatment in a reducing atmosphere, such as helium or argon.

Other methods for preparing inorganic phosphor dopants (100) include sol-gel synthesis, colloidal synthesis, and co-precipitation. In a sol-gel process, for example, the powders are weighed out and dissolved in concentrated acid, such as $HNO_3$ (such as 70% w/w), and then diluted with deionized water. This solution may then be cooled to room-temperature and added dropwise to a cold-saturated aqueous solution of another acid, such as oxalic acid. A solid material will then be allowed to precipitate and then washed with deionized water and other polar solvents (such as acetone, acetonitrile, dimethylformamide (DMF), dimethylsulfoxide (DMSO), isopropanol, or methanol). The solid material will then undergo calcination at a temperature of about 1000° C. to 1200° C. for several hours, followed by intermittent grinding and sintering. In certain examples, after weighing and mixing, the metal oxide host powder and rare earth oxide powder are directly placed in a furnace at 1000-1100° C. for 2-48 hours.

The prepared inorganic phosphor dopants (100) are then inserted into the substrate (host) material (101). The substrate (host) material (101) is in some examples a synthetic polymer substrate host material. The synthetic polymer substrate host material can be purchased from a commercial supplier, such as Dupont or Sigma. The inorganic phosphor dopant (100) is a powder, and can be incorporated into the substrate material (101) by melting the polymer substrate and then mixing in the inorganic phosphor dopant (100). The mixing can be facilitated, for example, by further heating the material, and/or by using a mixing paddle. An amount of inorganic phosphor dopant (100) sufficient for disinfection of the substrate surface (101*a*) can be incorporated into the synthetic polymer substrate (host) material (101).

After the inorganic phosphor dopant (100) is incorporated into the substrate material (101), the photon-emitting inorganic phosphor-doped (synthetic polymer) substrate material is cured. Curing can proceed, for example, at room temperature in air. Curing allows the photon-emitting inorganic phosphor-doped (synthetic polymer) substrate material to harden with the inorganic phosphor dopants (100) dispersed throughout the substrate (polymer host) material (101). The smaller the difference in polarity between the substrate (polymer host) material (101) and the inorganic phosphor dopant (100), the more homogeneously dispersed the inorganic phosphor dopant (100) will be throughout the polymer.

Further, the disclosure comprises examples according to the following clauses:

Clause 1. A method for disinfecting a surface, comprising:
- exposing a surface of a substrate material comprising an inorganic phosphor dopant to a UV light source;
- wherein the exposing causes the inorganic phosphor dopant in the substrate material to emit photons; and
- wherein the photons irradiate the surface, thereby disinfecting the surface.

Clause 2. The method of clause 1, wherein the inorganic phosphor dopant in the substrate material emits photons with a wavelength of light between about 200 nm and 280 nm.

Clause 3. The method of clause 2, wherein the inorganic phosphor dopant in the substrate material emits photons with a wavelength of light between about 225 nm and 250 nm.

Clause 4. The method of any of clauses 1-3, wherein the UV light source has a wavelength between about 160 nm and 320 nm.

Clause 5. The method of any of clauses 1-4, wherein the UV light source has a wavelength of about 222 nm, 254 nm, or 275 nm.

Clause 6. The method of any of clauses 1-5, wherein the inorganic phosphor dopant is a metal oxide or metal fluoride comprising a rare earth ion selected from the group consisting of $Pr^{3+}$, $Ce^{3+}$, $Eu^{3+}$, $Eu^{2+}$, $Gd^{3+}$, $Tb^{3+}$, and $Dy^{3+}$, or a mixture thereof.

Clause 7. The method of clause 6, wherein the rare earth ion is $Pr^{3+}$.

Clause 8. The method of clause 6 or 7, wherein the metal oxide is selected from the group consisting of silicates, phosphates, borates, oxides, oxynitrides, oxysulfides, and aluminates, or combinations thereof.

Clause 9. The method of any of clauses 1-8, wherein the substrate material comprises one or more synthetic polymers.

Clause 10. The method of clause 9, wherein the substrate material comprises a material selected from the group consisting of optionally fluorinated thermoplastics, thermosetting resins, and electronegative resins.

Clause 11. The method of clause 9 or 10, wherein the substrate material comprises a material selected from the group consisting of tetrafluoroethylene, polyvinyl fluoride, polyurethane, polyester, epoxy, phenolic, vinyl ester, polyamide, polyamide-imide, polyether imide, polyvinylchloride, polyether ketone ketone, polycarbonate, polyphenylsulphone, polymethylmethacrylate, polyacrylate, and benzoxazine.

Clause 12. The method of any of clauses 1-11, wherein the exposing the substrate material comprising the inorganic phosphor dopant to a UV light source is for a time sufficient to charge the inorganic phosphor dopant in the substrate material.

Clause 13. The method of any of clauses 1-12, wherein the UV light source is a pulsed Xenon-ultraviolet device.

Clause 14. A photon-emitting inorganic phosphor-doped substrate material, comprising: a substrate material comprising an inorganic phosphor dopant, wherein the inorganic phosphor dopant in the substrate material is capable of emitting photons upon exposure of a surface of the photon-emitting inorganic phosphor-doped substrate material to a UV light source.

Clause 15. The photon-emitting inorganic phosphor-doped substrate material of clause 14, wherein the substrate material comprises one or more synthetic polymers.

Clause 16. The photon-emitting inorganic phosphor-doped substrate material of clause 14 or 15, wherein the substrate material comprises a material selected from the group consisting of optionally fluorinated thermoplastics, thermosetting resins, and electronegative resins.

Clause 17. The photon-emitting inorganic phosphor-doped substrate material of any of clauses 14-16, wherein the substrate material comprises a material selected from the group consisting of tetrafluoroethylene, polyvinyl fluoride, polyurethane, polyester, epoxy, phenolic, vinyl ester, polyamide, polyamide-imide, polyether imide, polyvinylchloride, polyether ketone ketone, polycarbonate, polyphenylsulphone, polymethylmethacrylate, polyacrylate, and benzoxazine.

Clause 18. The photon-emitting inorganic phosphor-doped substrate material of any of clauses 14-17, wherein the inorganic phosphor dopant is a metal oxide or metal fluoride comprising a rare earth ion selected from the group consisting of $Pr^{3+}$, $Ce^{3+}$, $Eu^{3+}$, $Eu^{2+}$, $Gd^{3+}$, $Tb^{3+}$, and $Dy^{3+}$, or a mixture thereof.

Clause 19. The photon-emitting inorganic phosphor-doped substrate material of clause 18, wherein the rare earth ion is $Pr^{3+}$.

Clause 20. The photon-emitting inorganic phosphor-doped substrate material of clause 18 or 19, wherein the metal oxide is selected from the group consisting of silicates, phosphates, borates, oxides, oxynitrides, oxysulfides, and aluminates, or combinations thereof.

Clause 21. The photon-emitting inorganic phosphor-doped substrate material of any of clauses 14-20, wherein the inorganic phosphor dopant in the substrate material is capable of emitting photons with a wavelength of light between about 180 nm and 320 nm upon exposure of a surface of the photon-emitting inorganic phosphor-doped substrate material to a UV light source.

Clause 22. A method for preparing a photon-emitting material for surface disinfection, comprising:

contacting a substrate material with an inorganic phosphor dopant to prepare a photon-emitting inorganic phosphor-doped substrate material, wherein the inorganic phosphor dopant in the photon-emitting inorganic phosphor-doped substrate material is capable of emitting photons upon exposure of a surface of the inorganic phosphor-doped substrate material to a UV light source.

Clause 23. The method of clause 22, wherein the inorganic phosphor dopant in the photon-emitting inorganic phosphor-doped substrate material is capable of emitting photons with a wavelength of light between about 180 nm and 320 nm.

Clause 24. The method of clause 22 or 23, wherein the inorganic phosphor dopant is a metal oxide or metal fluoride comprising a rare earth ion selected from the group consisting of $Pr^{3+}$, $Ce^{3+}$, $Eu^{3+}$, $Eu^{2+}$, $Gd^{3+}$, $Tb^{3+}$, and $Dy^{3+}$, or a mixture thereof.

Clause 25. The method of clause 24, wherein the rare earth ion is $Pr^{3+}$.

Clause 26. The method of clause 24 or 25, wherein the metal oxide is selected from the group consisting of silicates, phosphates, borates, oxides, oxynitrides, oxysulfides, and aluminates, or combinations thereof.

Clause 27. The method of any of clauses 22-26, wherein the substrate material comprises one or more synthetic polymers.

Clause 28. The method of clause 27, wherein the substrate material comprises a material selected from the group consisting of optionally fluorinated thermoplastics, thermosetting resins, and electronegative resins.

Clause 29. The method of clause 27 or 28, wherein the substrate material comprises a material selected from the group consisting of tetrafluoroethylene, polyvinyl fluoride, polyurethane, polyester, epoxy, phenolic, vinyl ester, polyamide, polyamide-imide, polyether imide, polyvinylchloride, polyether ketone ketone, polycarbonate, polyphenylsulphone, polymethylmethacrylate, polyacrylate, and benzoxazine.

The following examples are offered by way of illustration and not by way of limitation. Those skilled in the art will appreciate that other synthetic routes may be used to synthesize the inorganic phosphor dopants and inorganic phosphor-doped substrate materials described herein. Although specific starting materials and reagents are depicted and discussed in the Examples, other starting materials and reagents can be easily substituted to provide a variety of derivative materials and/or reaction conditions. In addition, many of the exemplary materials prepared by the described methods can be further modified in light of this disclosure using conventional chemistry well known to those skilled in the art.

EXAMPLES

Example 1: Preparation of Photon-Emitting Inorganic Phosphor-Doped Substrate Material ($Ca_{2-x}Al_2SiO_{7:x}Pr^{3+}$-Doped Polyvinyl Fluoride)

Step 1. Preparation of $Ca_{2-x}Al_2SiO_{7:x}Pr^{3+}$ (100)

CaO, $Al_2O_3$, $SiO_2$, and $Pr_6O_{11}$ are purchased from Sigma Aldrich. CaO, $Al_2O_3$, $SiO_2$, and $Pr_6O_{11}$ are weighed out such that the amount of $Pr_6O_{11}$ in the mixture will yield a 0.5-5% substitution by praseodymium on the calcium site. The powders are then ground using an agate mortar and pestle for approximately five minutes, until the powders form a gray, fine mixture. Following this, the mixed powder is placed in a ceramic alumina crucible and pre-fired in air at 900° C. for two hours. Following this, the mixed powder is ground up in an agate mortar and pestle for approximately three minutes. The mixed powder is then placed back in the alumina crucible and in a furnace for heating at 1300° C. in air for seven hours. The powders are removed from the furnace and allowed to cool to room temperature.

The prepared $Ca_{2-x}Al_2SiO_{7:x}Pr^{3+}$ inorganic phosphor dopant (100) is analyzed by powder X-ray diffraction. The crystal structure is solved using FullProf to verify the Ca/Pr site mixing in the $Ca_2Al_2SiO_7$ crystal structure.

Step 2. Preparation of $Ca_{2-x}Al_2SiO_{7:x}Pr^{3+}$-doped Polyvinyl Fluoride Polyvinyl fluoride (Dupont) (101) is heated under an Argon atmosphere to about 180° C., allowing the material to melt. The $Ca_{2-x}Al_2SiO_{7:x}Pr^{3+}$ (100) powder prepared in Step 1 is thoroughly mixed with the melted polyvinyl fluoride in an amount of about 10% volume phosphor/volume polymer, such that the $Ca_{2-x}Al_2SiO_{7:x}Pr^{3+}$ is uniformly incorporated into the polyvinyl fluoride host material (101). The doped polyvinyl fluoride is then allowed to cure, forming a solidified $Ca_{2-x}Al_2SiO_{7:x}Pr^{3+}$-doped polyvinyl fluoride substrate material. In certain examples, the $Ca_{2-x}Al_2SiO_{7:x}Pr^{3+}$-doped polyvinyl fluoride substrate material can be shaped while it cures, using, for example, a mold. The mold can assist with configuring the $Ca_{2-x}Al_2SiO_{7:x}Pr^{3+}$-doped polyvinyl fluoride substrate material into a usable product, such as a cabinet, countertop, wall covering, or cover for a variety of household, healthcare, automobile, or aeronautic products. Additionally, after the solidified $Ca_{2-x}Al_2SiO_{7:x}Pr^{3+}$-doped polyvinyl fluoride substrate material is prepared, the material can be easily shaped and modified, for example, using a saw, sandpaper, or a suitable mold.

Example 2: Disinfection Using Inorganic Phosphor-Doped Substrate Material ($Ca_{2-x}Al_2SiO_{7:x}Pr^{3+}$-Doped Polyvinyl Fluoride)

The $Ca_{2-x}Al_2SiO_{7:x}Pr^{3+}$-doped polyvinyl fluoride substrate material prepared in Step 2 is exposed to a UV lamp having a wavelength between about 160 nm and 280 nm. This is the radiant excitation energy for the $Ca_{2-x}Al_2SiO_{7:x}Pr^{3+}$ phosphors (100) in the polyvinyl fluoride host substrate material (101). The $Ca_{2-x}Al_2SiO_{7:x}Pr^{3+}$-doped polyvinyl fluoride substrate material is exposed to the UV light source (104), such as a UV lamp, for approximately two minutes to ten minutes, allowing the $Ca_{2-x}Al_2SiO_{7:x}Pr^{3+}$ phosphors (100) to charge. The UV lamp is then turned off. The $Ca_{2-x}Al_2SiO_{7:x}Pr^{3+}$ phosphors (100) in the polyvinyl fluoride substrate (host) material (101) then emit light in the range of 200 nm to 280 nm for about two to ten minutes. This range of light emission corresponds with UV-C light, which is known to be germicidal. The germicidal light emitted by the $Ca_{2-x}Al_2SiO_{7:x}Pr^{3+}$ phosphors in the substrate material irradiates the surface (101*a*) of the $Ca_{2-x}Al_2SiO_{7:x}Pr^{3+}$-doped polyvinyl fluoride substrate material, thereby disinfecting the surface (101*a*). A spectrofluorometer is used to measure the afterglow intensity of the phosphor-doped substrate material.

In another example, a UV light source (104) can be a pulsed Xenon-ultraviolet device having a wavelength of about 222 nm, 254 nm, or 275 nm is exposed to the $Ca_{2-x}Al_2SiO_{7:x}Pr^{3+}$-doped polyvinyl fluoride substrate material prepared in Step 2. In one example, a surface (101*a*) of the $Ca_{2-x}Al_2SiO_{7:x}Pr^{3+}$-doped polyvinyl fluoride substrate material is exposed to a pulsed Xenon-ultraviolet device having a 254 nm wavelength for approximately two minutes. When the excitation light is removed, UV-C persistent luminescence emission at 268 nm is obtained. The observation of $Pr^{3+}$ UV-C afterglow in the $Ca_{2-x}Al_2SiO_{7:x}Pr^{3+}$-doped polyvinyl fluoride material suggests that the energy traps in the $Ca_{2-x}Al_2SiO_{7:x}Pr^{3+}$ phosphors (100) can be effectively filled by 254 nm light excitation and that the energy traps are located at appropriate energy positions so that they can efficiently capture electrons from the $Pr^{3+}$ $4f^15d^1$ state during the excitation and release the electrons back to the $4f^15d^1$ state due to ambient thermal stimulation after the excitation ceases. The isotropic light emission effectively disinfects the surface (101*a*) of the $Ca_{2-x}Al_2SiO_{7:x}Pr^{3+}$-doped polyvinyl fluoride substrate material. A spectrofluorometer is used to measure the afterglow intensity of the phosphor-doped substrate material.

Example 3: Preparation of Photon-Emitting Inorganic Phosphor-Doped Substrate Material ($NaY_{(1-x)}F_{6:x}Pr^{3+}$-Doped Tetrafluoroethylene)

Step 1: Preparation of $NaY_{(1-x)}F_{6:x}Pr^{3+}$ (100)

Pr-doped polycrystalline fluoride elpasolite phosphors, with nominal compositions of $Cs_2NaY_{(1-x)}F_{6:x}Pr^{3+}$ (wherein x=0.01-0.10), are prepared by solid-state synthesis. $Cs_2CO_3$ (1.6290 g, 99.99%, Aladdin, Shanghai, China), $NaHCO_3$, (0.4200 g, 99.99%, Aladdin, Shanghai, China), $Y_2O_3$, (0.5588 g, 99.99%, Aladdin, Shanghai, China), $NH_4F$ (2.2222 g, 99.99%, Aladdin, Shanghai, China), and $Pr_6O_{11}$ (0.0085 g, 99.996%, Alfa, United States) powders are mixed together with 3 mL of acetone and then ground thoroughly for about five minutes. The obtained powders are thermally treated at 150° C. in air for 7 h, followed by regrinding to obtain a fine powder. The mixture is then sintered at 450° C. for 30 min in air. The obtained powders are then reground, followed by sintering at 700° C. for 10 h under a nitrogen atmosphere. Corundum boats with a purity of 99% and a platinum crucible are used as vessels for the above synthesis.

The prepared $Cs_2NaY_{(1-x)}F_{6:x}Pr^{3+}$ inorganic phosphor dopant (100) is analyzed by powder X-ray diffraction. The crystal structure is solved using FullProf to verify the Y/Pr site mixing in the $Cs_2NaY_{(1-x)}F_{6:x}Pr^{3+}$ crystal structure. The structure crystalizes in a Fm-3m space group that corresponds to the cubic elpasolite. In this double perovskite structure, both Y and Na coordinate with six fluorine atoms, and doped $Pr^{3+}$ ions substitute for $Y^{3+}$ ions.

Step 2. Preparation of $Cs_2NaY_{(1-x)}F_{6:x}$Pr-doped Tetrafluoroethylene Tetrafluoroethylene (Dupont), a substrate (host) material (101), is heated under an Argon atmosphere to about 327° C., allowing the material to melt. The $Cs_2NaY_{(1-x)}F_{6:x}Pr^{3+}$ (100) powder prepared in Step 1 is thoroughly mixed with the melted tetrafluoroethylene in an amount of about 10% volume phosphor/volume polymer, such that the $Cs_2NaY_{(1-x)}F_{6:x}Pr^{3+}$ is uniformly incorporated into the tetrafluoroethylene substrate (host) material (101). The doped tetrafluoroethylene is then allowed to cure, forming a solidified $Cs_2NaY_{(1-x)}F_{6:x}Pr^{3+}$-doped tetrafluoroethylene substrate material. In certain examples, the $Cs_2NaY_{(1-x)}F_{6:x}Pr^{3+}$-doped tetrafluoroethylene substrate material can be shaped while it cures, using, for example, a mold. The mold can assist with configuring the $Cs_2NaY_{(1-x)}F_{6:x}Pr^{3+}$-doped tetrafluoroethylene substrate material into a usable product, such as a cabinet, countertop, wall covering, or cover for a variety of household, healthcare, automobile, or aeronautic products. Additionally, after the solidified $Cs_2NaY_{(1-x)}F_{6:x}Pr^{3+}$-doped tetrafluoroethylene substrate material is prepared, the material can be easily shaped and modified, for example, using a saw, sandpaper, or a suitable mold.

Example 4: Disinfection Using Inorganic Phosphor-Doped Substrate Material ($Cs_2NaY_{(1-x)}F_{6:x}Pr^{3+}$-Doped Tetrafluoroethylene)

The $Cs_2NaY_{(1-x)}F_{6:x}Pr^{3+}$-doped tetrafluoroethylene substrate material prepared in Step 2 is exposed to pulsed Xenon lamp for approximately 30 seconds having a wavelength between 100 nm and 225 nm. The pulsed light is sufficient to charge the $Cs_2NaY_{(1-x)}F_{6:x}Pr^{3+}$ phosphors (100) in the tetrafluoroethylene host substrate material (101). The $Cs_2NaY_{(1-x)}F_{6:x}Pr^{3+}$ phosphors (100) in the tetrafluoroethylene substrate (host) material (101) then emit light in the range of 200 nm to 280 nm (germicidal light) for about ten to twenty minutes. The germicidal light emitted by the $Cs_2NaY_{(1-x)}F_{6:x}Pr^{3+}$ phosphors in the substrate material isotropically irradiates the surface (101*a*) of the $Cs_2NaY_{(1-x)}F_{6:x}Pr^{3+}$-doped tetrafluoroethylene substrate material (101), thereby disinfecting the surface (101*a*). A spectrofluorometer is used to measure the afterglow intensity of the phosphor-doped substrate material.

Efforts have been made to ensure accuracy with respect to numbers used (e.g., amounts, temperature, etc.) but some experimental errors and deviations should be accounted for.

One skilled in the art will recognize many methods and materials similar or equivalent to those described herein, which could be used in practicing the subject matter described herein. The present disclosure is in no way limited to just the methods and materials described.

Where a range of values is provided, it is understood that each intervening value, to the tenth of the unit of the lower limit, unless the context clearly dictates otherwise, between the upper and lower limit of the range and any other stated or intervening value in that stated range, is encompassed. The upper and lower limits of these small ranges which may independently be included in the smaller rangers is also encompassed, subject to any specifically excluded limit in the stated range. Where the stated range includes one or both of the limits, ranges excluding either or both of those included limits are also included.

Many modifications and other examples set forth herein will come to mind to one skilled in the art to which this subject matter pertains having the benefit of the teachings presented in the foregoing descriptions and the associated drawings. Therefore, it is to be understood that the subject matter is not to be limited to the specific examples disclosed and that modifications and other examples are intended to be included within the scope of the appended claims. Although specific terms are employed herein, they are used in a generic and descriptive sense only and not for purposes of limitation.

The invention claimed is:

1. A method for disinfecting a surface, comprising:

exposing a surface of a substrate material comprising an inorganic phosphor dopant to a UV light source;

wherein the inorganic phosphor dopant comprises $Ca_2Al_2SiO_7$ doped with $Pr^{3+}$;

wherein said exposing causes said inorganic phosphor dopant in said substrate material to emit photons; and wherein said photons irradiate said surface, thereby disinfecting said surface.

2. The method of claim 1, wherein said inorganic phosphor dopant in said substrate material emits photons with a wavelength of light between about 200 nm and 280 nm.

3. The method of claim 1, wherein said UV light source has a wavelength between about 160 nm and 320 nm.

4. The method of claim 1, wherein said inorganic phosphor dopant further comprises a metal oxide or metal fluoride comprising a rare earth ion selected from the group consisting of $Ce^{3+}$, $Eu^{3+}$, $Eu^{2+}$, $Gd^{3+}$, $Tb^{3+}$, and $Dy^{3+}$, or a mixture thereof.

5. The method of claim 4, wherein said metal oxide is selected from the group consisting of silicates, phosphates, borates, oxides, oxynitrides, oxysulfides, and aluminates, or combinations thereof.

6. The method of claim 1, wherein said substrate material comprises one or more synthetic polymers.

7. The method of claim 1, wherein said exposing said substrate material comprising said inorganic phosphor dopant to a UV light source is for a time sufficient to charge said inorganic phosphor dopant in said substrate material.

8. A photon-emitting inorganic phosphor-doped substrate material, comprising:

a substrate material comprising an inorganic phosphor dopant, wherein said inorganic phosphor dopant in said substrate material is capable of emitting photons upon exposure of a surface of said photon-emitting inorganic phosphor-doped substrate material to a UV light source; and wherein the inorganic phosphor dopant comprises $Ca_2Al_2SiO_7$ doped with $Pr^{3+}$.

9. The photon-emitting inorganic phosphor-doped substrate material of claim 8, wherein said substrate material comprises one or more synthetic polymers.

10. The photon-emitting inorganic phosphor-doped substrate material of claim 9, wherein said substrate material comprises a material selected from the group consisting of fluorinated thermoplastics, thermosetting resins, and electronegative resins.

11. The photon-emitting inorganic phosphor-doped substrate material of claim 9, wherein said substrate material further comprises a material selected from the group consisting of tetrafluoroethylene, polyvinyl fluoride, polyurethane, polyester, epoxy, phenolic, vinyl ester, polyamide, polyamide-imide, polyether imide, polyvinylchloride, polyether ketone ketone, polycarbonate, polyphenylsulphone, polymethylmethacrylate, polyacrylate, and benzoxazine.

12. The photon-emitting inorganic phosphor-doped substrate material of claim 8, wherein said inorganic phosphor dopant further comprises a metal oxide or metal fluoride comprising a rare earth ion selected from the group consisting of $Ce^{3+}$, $Eu^{3+}$, $Eu^{2+}$, $Gd^{3+}$, $Tb^{3+}$, and $Dy^{3+}$, or a mixture thereof.

13. The photon-emitting inorganic phosphor-doped substrate material of claim 8, wherein said inorganic phosphor dopant in said substrate material is capable of emitting photons with a wavelength of light between about 200 nm and 280 nm upon exposure of a surface of said photon-emitting inorganic phosphor-doped substrate material to a UV light source.

14. A method for preparing a photon-emitting material for surface disinfection, comprising:

contacting a substrate material with an inorganic phosphor dopant to prepare a photon-emitting inorganic phosphor-doped substrate material, wherein said inorganic phosphor dopant in said photon-emitting inorganic phosphor-doped substrate material is capable of emitting photons upon exposure of a surface of said photon-emitting inorganic phosphor-doped substrate material to a UV light source; and wherein the inorganic phosphor dopant comprises $Ca_2Al_2SiO_7$ doped with $Pr^{3+}$.

15. The method of claim 14, wherein said inorganic phosphor dopant in said photon-emitting inorganic phosphor-doped substrate material is capable of emitting photons with a wavelength of light between about 200 nm and 280 nm.

16. The method of claim 14, wherein said inorganic phosphor dopant further comprises a metal oxide or metal fluoride comprising a rare earth ion selected from the group consisting of $Ce^{3+}$, $Eu^{3+}$, $Eu^{2+}$, $Gd^{3+}$, $Tb^{3+}$, and $Dy^{3+}$, or a mixture thereof.

17. The method of claim 16, wherein said metal oxide is selected from the group consisting of silicates, phosphates, borates, oxides, oxynitrides, oxysulfides, and aluminates, or combinations thereof.

18. The method of claim 14, wherein said substrate material comprises one or more synthetic polymers.

19. The method of claim 18, wherein said substrate material comprises a material selected from the group consisting of fluorinated thermoplastics, thermosetting resins, and electronegative resins.

* * * * *